US012746091B2

(12) United States Patent
Zachmann et al.

(10) Patent No.: US 12,746,091 B2
(45) Date of Patent: Sep. 29, 2026

(54) ILLUMINATION DEVICE FOR ILLUMINATING A SURGICAL WOUND

(71) Applicant: Dr. Mach GmbH & Co. KG, Ebersberg (DE)

(72) Inventors: Gabriel Zachmann, Göttingen (DE); Andre Richard Mühlenbrock, Bremen (DE); Peter Kohrs, Meine (DE); Adrian Urs Fox, Ramerberg (DE)

(73) Assignee: DR. MACH GMBH & CO. KG, Ebersberg (DE)

( * ) Notice: Subject to any disclaimer, the term of this patent is extended or adjusted under 35 U.S.C. 154(b) by 225 days.

(21) Appl. No.: 18/690,489

(22) PCT Filed: Sep. 16, 2022

(86) PCT No.: PCT/EP2022/075824
§ 371 (c)(1),
(2) Date: Mar. 8, 2024

(87) PCT Pub. No.: WO2023/041732
PCT Pub. Date: Mar. 23, 2023

(65) Prior Publication Data

US 2024/0382282 A1 Nov. 21, 2024

(30) Foreign Application Priority Data

Sep. 17, 2021 (DE) ..................... 10 2021 124 083.2

(51) Int. Cl.
*A61B 90/35* (2016.01)
*A61B 90/00* (2016.01)
*F21W 131/205* (2006.01)

(52) U.S. Cl.
CPC .............. *A61B 90/35* (2016.02); *A61B 90/36* (2016.02); *F21W 2131/205* (2013.01)

(58) Field of Classification Search
CPC .............. A61B 2090/309; A61B 90/35; F21W 2131/20; F21W 2131/202; F21W 2131/205; F21W 2131/208
See application file for complete search history.

(56) References Cited

U.S. PATENT DOCUMENTS

2012/0075832 A1 3/2012 Schmid et al.
2014/0066722 A1 3/2014 Marka et al.
(Continued)

FOREIGN PATENT DOCUMENTS

DE 19839827 A1 3/2000
DE 102013012231 A1 1/2015
(Continued)

OTHER PUBLICATIONS

German Publication No. 102021124083.2, Office Action mailed May 17, 2022, 5 pages.
(Continued)

*Primary Examiner* — Sean P Gramling
(74) *Attorney, Agent, or Firm* — Kilpatrick Townsend & Stockton LLP

(57) ABSTRACT

Disclosed is an illumination device for illuminating a surgical wound, which has a wound opening area and a depth extension direction, the illumination device including a control device for inputting information about a position of the wound opening area and the depth extension direction, and a plurality of lighting devices where at least one of the lighting devices emits light such that an illuminated area at least partially overlapping with the wound opening area and where the lighting devices are arranged in the array in a substantially unchangeable position.

15 Claims, 2 Drawing Sheets

(56) References Cited

U.S. PATENT DOCUMENTS

Figure 1:
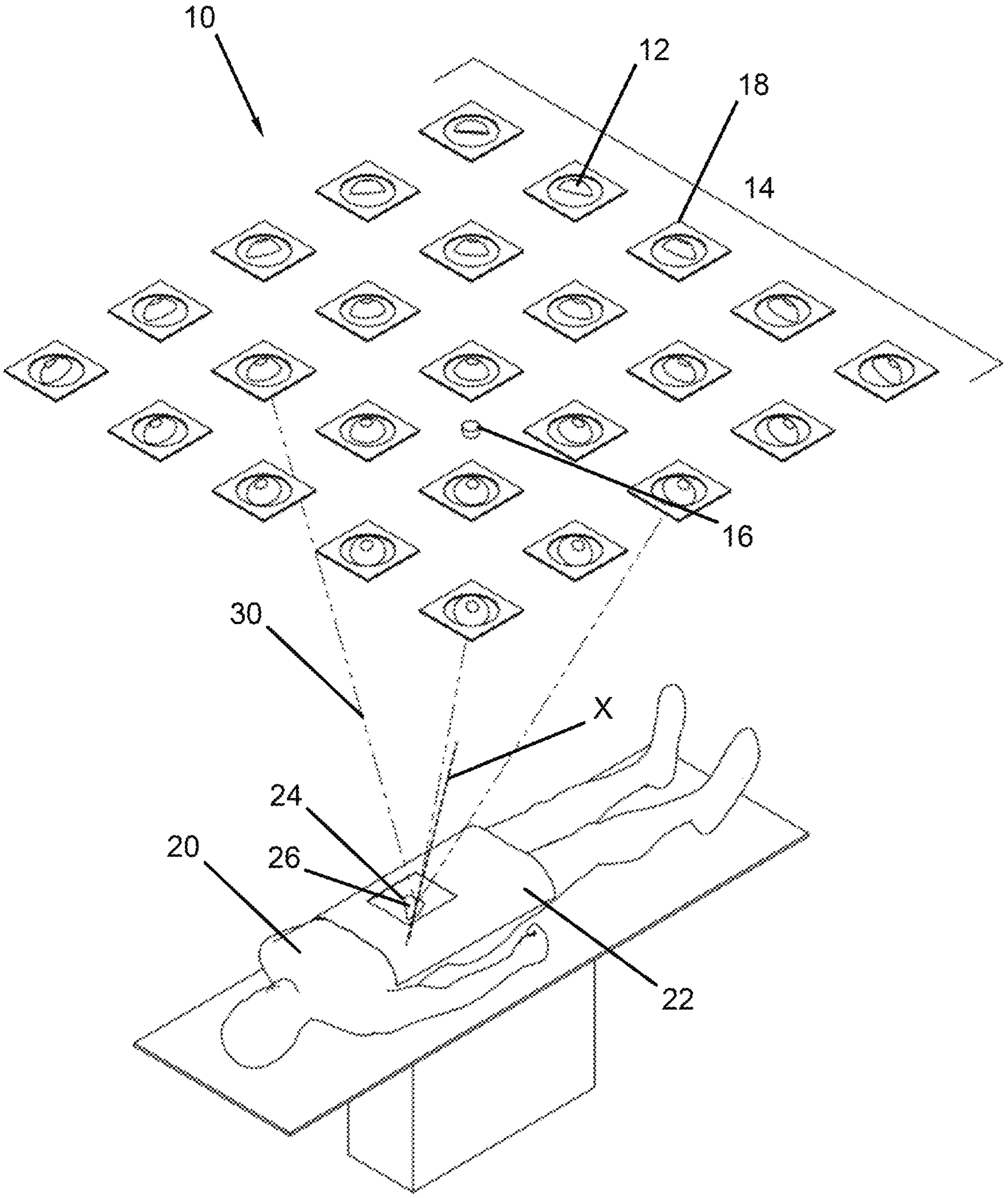

| | | | | |
|---|---|---|---|---|
| 2016/0174336 | A1 | 6/2016 | Elfring et al. | |
| 2021/0108783 | A1* | 4/2021 | Hallack .................. | A61B 90/30 |

FOREIGN PATENT DOCUMENTS

| | | | |
|---|---|---|---|
| EP | 2434202 | A1 | 3/2012 |
| EP | 2495487 | A1 | 9/2012 |

OTHER PUBLICATIONS

International Application No. PCT/EP2022/075824, International Search Report and Written Opinion mailed Jan. 5, 2033, 16 pages.

* cited by examiner

ILLUMINATION DEVICE FOR ILLUMINATING A SURGICAL WOUND

CROSS REFERENCE TO RELATED APPLICATIONS

This application is a U.S. national phase of International Patent Application No. PCT/EP2022/075824 filed on Sep. 16, 2022, which claims priority to German Patent Application No. 10 2021 124 083.2, filed in Germany on Sep. 17, 2021. The entire contents of both applications are incorporated herein by this reference.

The present invention relates to an illumination device for illuminating a surgical wound which has a wound opening area on the surface of the body of a patient and extends into the body of the patient in a depth extension direction.

In present day applications, the ideal illumination of a surgical wound, also called "situs," is achieved by the surgeon aligning the luminaire manually. On the one hand, this requires a complex mechanism for the luminaires and, on the other hand, surgeons must interrupt their actual activity for each readjustment of the luminaire. This extends the surgery time and thus represents an additional burden for the patient.

It is therefore the object of the present invention to provide an illumination device that can be adjusted in a simplified manner and can be adapted, in particular automatically, to changing conditions during surgery.

This object is achieved by an illumination device for illuminating a surgical wound, wherein the illumination device comprises a control device with means for inputting information about a position of the wound opening area and the depth extension direction in a spatial coordinate system, wherein the illumination device has a plurality of lighting devices which are each configured to emit light in a main emission direction and which each have at least one illuminant, wherein at least one of the lighting devices is configured to emit light such that an area illuminated by said at least one lighting device at least partially overlaps with the wound opening area, wherein the main emission direction of each lighting device, which has an illuminated area at least partially overlapping with the wound opening area, and the depth extension direction of the surgical wound each enclose an angle with one another, the value of which does not exceed a predetermined angular value, wherein at least those light devices that have an illuminated area at least partially overlapping with the wound opening area and whose respective main emission direction does not exceed a predetermined angular value with the depth extension direction of the surgical wound form an array, wherein the lighting devices are arranged in the array in a substantially unchangeable position in relation to the spatial coordinate system.

In this way, it can be achieved that light emitted by a plurality of lighting devices coincides with a corresponding situs, so that an illuminance of the situs through the illumination device can be increased compared to a single lighting device, and also that the light is directed such that it can reach up to the bottom of a narrow, deep surgical wound to provide a sufficiently high illuminance with simultaneous avoidance of disturbing shadowing. In particular, a homogeneous illumination of the situs can thus be achieved.

It should already be mentioned at this point that the term "emitted light" can relate to the light directly emitted by the lighting device or to the light reflected directly from a reflector associated with the lighting device, in particular, in combination with the light directly emitted by the lighting device, depending on the design of the lighting device.

The main emission direction may be arranged on a central axis of a light cone of a corresponding lighting device. Of course, it is also conceivable to place a corresponding central axis into the light emitted by a corresponding lighting device, which light is not radiated conically. Preferably, focal points of mutually parallel cross sections of a light beam emitted by a corresponding lighting device or reflected by a reflector associated with a corresponding lighting device can be connected to one another to form the corresponding central axis.

The angle between a corresponding main emission direction and the depth extension direction of the surgical wound may be formed between a projection of a corresponding main emission direction and the depth extension direction of the surgical wound in a plane which comprises the depth extension direction of the surgical wound and a center of a corresponding lighting device. Corresponding angular values between a corresponding main emission direction and the depth extension direction of the surgical wound can thus also be formed in the event that the main emission direction and the depth extension direction do not intersect, i.e., are skewed in relation to one another.

The predetermined region of the angle can advantageously be from 0° to 75°, in particular from 0° to 60°, particularly preferably from 0° to 45°.

The lighting devices may comprise at least one LED and/or at least one laser source. Due to their low heat development, such light sources are preferred so that a climate prevailing in an operating room is not impaired or is only slightly impaired.

Advantageously, the control device may be configured to control only those lighting devices of the illumination device having an area at least partially overlapping the wound opening area, which lighting devices enclose a mutual angle between their corresponding main emission direction and the depth extension direction of the surgical wound, the value of which angle does not exceed the predetermined angle value. It can thus be avoided that lighting devices whose corresponding main emission direction exceeds the predetermined angular value do not contribute to the illumination of the situs to prevent an intensity drop in the depth extent of the surgical wound.

In a development of the present invention, the illumination device may comprise air passages which are configured to allow an air flow of an air-conditioning ceiling to which the illumination device is attached or in which the illumination device is integrated. In this way, the illumination device can be installed in operating rooms without impairing the laminar air flow, which usually prevails in a surgical area.

Advantageously, the lighting devices may comprise light illuminants emitting light of different spectra and may be configured to emit light in an adjustable spectral range by mixing the light emitted by the illuminants. Depending on the surgery to be performed, it may be desired to adapt the spectral range of the surgical lighting, for example into a rather bluish or rather reddish lighting. Furthermore, it may be conceivable, to activate, alternatively or in addition to illumination in a visible spectral range, illumination of the situs in a non-visible spectral range, such as an ultraviolet and/or infrared spectral range, for example.

Furthermore, the lighting devices and/or individual illuminants of the lighting devices may be adjustable in their luminous flux. For example, individual lighting devices can thus be dimmed to reduce an illumination of, for example, strongly reflective regions, and thus regions that are glaring, outside the situs, through which surgeons could be impaired in their activity.

The lighting devices may comprise reflectors and/or optical lenses and/or optical conversion media which are configured to focus and/or scatter and/or deflect light and/or to change it spectrally. The reflectors and/or optical lenses can be displaceable and/or pivotable relative to the corresponding illuminant, in particular, using a piezo drive. Piezo drives are particularly suitable for the displacement in the submillimeter range, so that, for example, even the smallest focus can be set.

Furthermore, the illumination device may comprise an adjusting device which is configured up to set the angle between the main emission direction of at least one lighting devices and the depth extension direction of the surgical wound. The adjusting device of the illumination device can simulate the manual detection of a conventional surgical lamp on its handle and the setting of it relative to the surgical wound. For this purpose, the adjusting device may be connected to the control device.

For this purpose, the adjusting device may comprise a camera which is configured to detect regions located in the main emission direction of at least one lighting device, and a determination unit, or be connected thereto, which determination unit is configured to determine a surgical wound based on the regions detected by the camera, wherein the adjusting device is configured to change, in particular to reduce, the angle between the main emission direction of at least one lighting device and the depth extension direction of the surgical wound, in particular automatically. If, for example, a illumination device is used that has such a large number of lighting devices that only a selection of lighting devices has to be activated to sufficiently illuminate the surgical wound, the adjusting device can also automatically select lighting devices from all available lighting devices of the illumination device to minimize the angle between a common main emission direction of the selected lighting devices, which, for example, can lie on a central axis or a priority axis of the bundle of individual main emission directions of the selected lighting devices, and the depth extension direction of the surgical wound. For example, when the patient is moved, those lighting devices of the illumination device that optimally illuminate the surgical wound can thus automatically be reselected.

Furthermore, the adjusting device may comprise a camera which is configured to detect gestures which a user of the illumination device carries out, and a determination unit, or be connected thereto, which is configured to assign the gestures to predetermined operating commands, wherein the adjusting device is configured to set an alignment of a corresponding main emission direction of the lighting devices associated with the adjusting device as a result of the operating commands. For example, the surgeon can draw a line in the air with a finger, whereby the illumination device is caused to align the individual main emission directions or the common main emission direction, as described above, of the selected lighting devices coaxially or parallel to this line. Alternatively or additionally, the adjusting device may be controllable via voice input, for example using audible commands by the surgeon.

The adjusting device may also comprise, or be connected to, a data interface which is configured to receive surgery data relating to a surgery to be carried out on a patient, wherein the adjusting device is configured to adjust an alignment of a corresponding main emission direction from the lighting devices associated with the adjusting device on the basis of the surgery data. The surgery data can, for example, show themselves and/or in connection with a corresponding database, in which way a depth extension of a situs is produced in the course of the surgery. The illumination device can, on this basis, already select those lighting devices for illuminating the situs before the start of the surgery that are still suitable for illumination of the situs even with advanced surgery progression. It can thus be avoided that the selection of the lighting devices of the illumination device for illuminating the situs is changed during the surgery in a manner that negatively affects the surgeon, for example, due to changing shadow formation.

For example, the adjusting device may comprise an input device which comprises a pin-like portion connected to a base, wherein an angle of a longitudinal axis of the pin-like portion can be changed relative to the base, wherein the adjusting device may be configured to adjust an alignment of a corresponding main emission direction of a longitudinal axis associated with the adjusting device based on the angle of the pin-like portion to the base. The input device may be connected to the adjusting device wirelessly, wired or also via an articulated arrangement.

The adjusting device may be configured to individually set an alignment of a corresponding main emission direction of the lighting devices associated with the adjusting device based on the angle of the pin-like portion relative to the base, or to transfer a relative angle change of the angle of the pin-like portion to the base to any angle between a corresponding main emission direction of the lighting devices associated with the adjusting device and the depth extension direction of the surgical wound. To select corresponding lighting devices which the surgeon desires, the input device may additionally comprise a keypad which, for example, corresponds completely or in a reduced manner to the arrangement of lighting devices on the illumination device.

It is possible for the adjusting device to comprise an input device which comprises a pin-like portion which has a longitudinal axis and a detection unit which is configured to detect the position and orientation of the longitudinal axis of the pin-like portion of the input device in space and to output it to the adjusting device, wherein the adjusting device may be configured to adjust an alignment of a corresponding main emission direction of lighting devices associated with the adjusting device, based on the detected position and orientation of the longitudinal axis of the pin-like portion of the input device in space. The input device can either be connected to the base or can be freely positionable in space by it.

The input device may comprise a rangefinder which is configured to measure a distance of a distal end of the pin-like portion of the input device to the surgical wound and to output it to the adjusting device, wherein the adjusting device may be configured to set a focus of lighting devices associated with the adjusting device based the measured distance. By removing or approaching the input device relative to the situs, the illumination device can be prompted to defocus or focus light emitted by the selected lighting devices.

The detection unit may comprise a position sensor, in particular a gyroscope. In particular, the position sensor may serve to detect the position and/or orientation of the input device. The position sensor may be arranged in the pin-like portion of the input device.

In a development of the present invention, the detection unit may comprise a navigation device which is configured to recognize a geometry of the input device known to the navigation device and to assign a position and orientation in space to the input device in relation to the known geometry. The detection unit may, for example, be designed such that it emits light, for example in the infrared range, and receives light reflected from the input device. Due to a known relation of the longitudinal axis of the input device to the light detected by the detection unit which is reflected by the input device, the detection unit and/or the adjusting device can determine the longitudinal axis of the input device in three-dimensional space and output corresponding commands for aligning a common or corresponding main emission direction of the lighting devices to drives associated with said lighting devices.

The known geometry of the input device may be formed by passive or active markers whose position is permanently connected or can be connected to the pin-like portion of the input device. In particular, the passive markers can be designed as retroreflective markers which reflect incident light according to the angle of incidence. In contrast, active markers emit light independently, for example, using LEDs.

Furthermore, the illumination device may comprise at least one camera, in particular a light density camera, which detects an illuminance of the surgical wound, and a tracking unit which changes the illumination device to a decrease or increase in the illuminance of the surgical wound detected by the camera such that the illuminance of the surgical wound remains constant. The illumination device according to the invention may thus be able to keep a predetermined illuminance of the surgical wound substantially constant even when a shading of some lighting devices in their beam path to the surgical wound (or when a shading object is removed) occurs.

The tracking unit may increase the luminous flux of the lighting devices that have an illuminated area at least partially overlapping the wound opening area. That is to say that those of the selected and activated lighting devices that have already illuminated the surgical wound before the occurrence of a shading and are not affected by the shading now illuminate the situs with an increased luminous flux, so that the illuminance of the surgical wound substantially corresponds to the illuminance before the occurrence of the shading. The lighting devices affected by the shading can also be reduced in their luminous flux to reduce shadowing resulting therefrom.

Additionally or alternatively, the tracking unit can activate further lighting devices of the illumination device, whose main emission direction is at an angle with the depth extension direction of the surgical wound outside the predetermined region. This means that in this case lighting devices are connected which are not used to illuminate the surgical wound prior to the occurrence of the shading of lighting devices used to illuminate the surgical wound. The selection of additional lighting devices which are to be activated to illuminate the surgical wound can, for example, be prioritized based on the angle from its main emission direction with the depth extension direction of the surgical wound. In general, it is preferred by surgeons to activate additional lighting devices, even though their angles with the depth extension direction of the surgical wound are outside of the predetermined region, then to work on a an insufficiently illuminated situs.

When activating additional light devices, the tracking unit can start with those lighting devices that have the smallest angle between their main emission direction and the depth extension direction of the surgical wound. It can thus be ensured that a good depth illumination of the surgical wound can continue to be achieved.

Furthermore, the tracking unit can activate a further array with lighting devices which is arranged separately from the array of the illumination device. In particular, a plane in which the lighting devices of the further array extend can be arranged at an angle to a plane in which the lighting devices of the above-mentioned array extend. For example, depending on the type of shading of the lighting devices, the further array can be activated such that an object which causes the shading no longer lies on the path of the light between a corresponding lighting devices and the surgical wound, so that said object can be "illuminated," so to speak, by the lighting devices of the further array.

The tracking unit can advantageously focus at least one light cone of a lighting device. An illuminance of a surgical wound can also be increased by focusing corresponding light cones if this is necessary.

In a development of the present invention, the illumination device may comprise a plurality of cameras which detect an illuminance of the surgical wound, and which are arranged such that their visual axes form a predetermined angle relative to one another on the surgical wound, which is suitable for compensating for a covering of a view of a first camera onto the surgical wound with a second camera. It can thereby be ensured that the automatic tracking or adaptation of the illuminance of the surgical wound can be realized even if one of the cameras, which detect an illuminance of the surgical wound, does not have a free view of the surgical wound.

The illumination device may furthermore comprise a distance measuring device which measures a distance of the illumination device from the surgical wound, wherein the illumination device focuses corresponding lighting devices onto the surgical wound based on the distance measurement. In this way, the illumination device can automatically react to changing surgery conditions, such as the lifting and lowering of an operating table, and ensure a constant illumination of the surgical wound.

Furthermore, the illumination device can perform automatic focusing of lighting devices until a proportion of the illuminated field of a corresponding lighting device which overlaps with the surgical wound is maximized relative to the entire illuminated field. In particular, regions of the lighting field can thus be reduced, which illuminate an environment of the situs, in which a drape is usually arranged which, due to its strong reflection, should not be illuminated strongly, if at possible.

According to one embodiment of the present invention, the illumination device may comprise a plurality of cameras which detect at least the surgical wound and comprise a combination unit, wherein the perspectives of the surgical wound and the entire surgical environment captured by the plurality of cameras are combined by the combination unit to form a three-dimensional model. Based on the three-dimensional model, the illumination device can identify a main emission direction of at least one lighting device, the light of which is at least partially prevented from reaching the surgical wound by an obstacle which is arranged between the illumination device and the surgical wound, and/or identifies a main emission direction of at least one lighting device, the light of which reaches the surgical wound despite an obstacle arranged between the illumination device and the surgical wound. By using the three-dimensional model, a position and/or size of the object, which, as described above, causes shading, can be unambiguously determined in space, so that lighting devices and, if applicable, adaptations to the illumination device to be carried out can be identified to "illuminate" the object, as mentioned above.

Based on the three-dimensional model and the at least one identified main emission direction, the illumination device can change, in particular, activate or deactivate, at least one lighting device to increase or lower an illuminance of the surgical wound. In particular in the case in which objects which are introduced into the beam path of at least one lighting device cause shading and thus a reduction in the illumination intensity of the wound, these lighting devices involved in the shading can be reduced or even deactivated in their intensity, and at least one of the remaining, currently activated lighting devices can be increased in its intensity and/or at least one additional lighting device can be activated.

The illumination device can also comprise a distance measuring device and/or a camera which detect/detects an object moving over the surgical wound, wherein a change in the illumination device can be carried out on the basis of the detected object to minimize shading of the surgical wound by the object. A direct correlation between the moving object causing shading and the adaptation of the illumination device can thereby be produced. As a result, the required effort for an accurate and rapidly reacting adaptation of the illumination device can be reduced.

In a third aspect, the present invention relates to a method for illuminating a surgical wound, wherein the method comprises the steps:

- providing a illumination device, in particular, a illumination device according to the invention, which has a plurality of lighting devices which are each configured to emit light in a main emission direction, wherein at least some of the lighting devices form an array in which the lighting devices are arranged in a substantially unchangeable position with respect to a spatial coordinate system,
- inputting information about a position of a surgical wound in the spatial coordinate system which has a wound opening area on the surface of the body of a patient,
- determining a depth extension direction of the wound into the body of the patient,
- determining at least one lighting device of the illumination device, which lighting device is configured to emit light such that an area illuminated by said at least one lighting device at least partially overlaps with the wound opening area, and that its main emission direction encloses an angle with the depth extension direction of the surgical wound, the value of which angle does not exceed a predetermined angular value, and
- activating the lighting devices determined in this way to illuminate the surgical wound.

It should be pointed out here already that all of the features, effects, and advantages described for the device according to the invention can also be applied to the method according to the invention, and vice versa.

The method may further comprise:

- setting the angle between the main emission direction of at least one lighting device and the depth extension direction of the surgical wound by pivoting the corresponding lighting devices. As set out with respect to the device, this can be done, for example, using an adjusting device.

The method may comprise changing the luminous flux and/or the emission spectrum of at least one of the lighting devices. In this way, an illumination intensity can be adapted to a current surgery situation. It is also conceivable that an intensity control of the lighting devices is carried out depending on the predetermined angle value between the main emission direction and the depth extension direction.

The method according to the invention may, in particular, also comprise:

- detecting regions which are located in the main emission direction of at least one lighting device by a camera,
- determining information about the position of the surgical wound in the spatial coordinate system based on the regions captured by the camera,
- setting, in particular reducing, the angle between the main emission direction of at least one lighting device and the depth extension direction of the surgical wound, in particular automatically.

Advantageously, the method according to the invention may also comprise:

- providing a data interface via which data is passed on to the illumination device,
- inputting surgery data, based on which a basic prediction of the position of the surgical wound in the spatial coordinate system is possible, in particular preoperatively, via the data interface to adjust an alignment of a corresponding main emission direction of at least one lighting device based on the surgery data.

Figure 2:
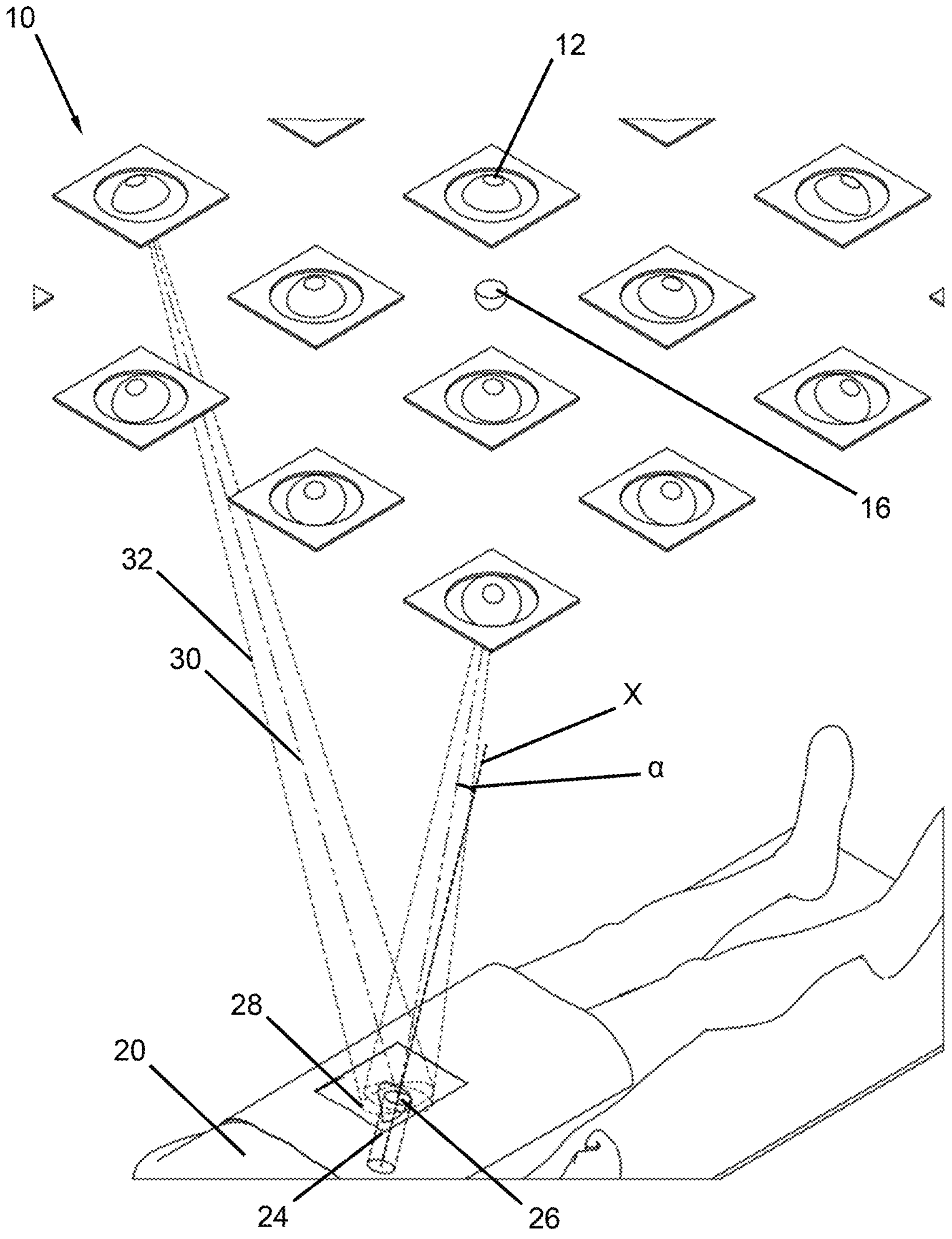

The present invention will be described in greater detail below by means of an embodiment with reference to the accompanying drawings. In the figures:

FIG. 1 depicts a perspective view of an surgical situation, wherein a surgical wound is illuminated by a illumination device according to the invention; and FIG. 2 depicts a detailed section from FIG. 1.

In FIG. 1, an illumination device according to the invention is generally designated by the reference sign 10. The illumination device 10 here comprises a plurality of lighting devices 12 which together form an array 14, and a camera 16. In the array 14 shown in FIG. 1, the individual lighting devices 12 are arranged in a square configuration of twenty-five lighting devices 12 and at equal distances from one another, so that air, for example from an air-conditioning ceiling of the operating room, can pass between the individual lighting devices 12. Each of the lighting devices 12 comprises at least one illuminant (not shown in detail in FIG. 1), for example in the form of at least one LED. However, the general arrangement of the lighting devices 12 is not limited to the variant shown in FIG. 1 so that a different number and/or other configuration of lighting devices 12 is also possible that is elliptical or rectangular, for example.

Each illuminant of a lighting device 12 is mounted pivotably relative to a holder 18 of the lighting device 12, in particular in combination with an associated reflector, wherein the corresponding lighting device 12 is connected to the ceiling of the operating room via the holder 18. To control a pivoting of the illuminant relative to the holder 18, in particular, at least one electric motor may be provided which is connected to a control device and is configured to displace the associated illuminant relative to the holder 18.

A patient 20 can also be seen in FIG. 1. In the context of a surgery to be carried out on the patient 20, the patient is covered with a drape 22, wherein a location (also called "surgical wound") 24 on the body of the patient 22 to be treated remains free. The surgical wound 24 has a wound opening area 26 on the skin of the patient 22 and a depth extension direction X along the wound channel running into the body of the patient 22.

In order for a surgeon to appropriately treat the patient, the surgical wound 24 must be sufficiently illuminated. For this purpose, lighting devices 12 are activated and adjusted such that an area 28 (see FIG. 2) illuminated by a corresponding lighting device 12 overlaps at least partially with the wound opening area 26. A main emission direction 30 can be assigned to each lighting device 12. With reference to FIG. 2, it can be seen that a corresponding main emission direction 30 can be the central axis of a light cone 32 which here extents conically from the illuminant to the wound opening area 26. According to the invention, only those lighting devices 12 are selected for illuminating the surgical wound 24 that have, with a corresponding adjustment, an illuminated area 28 that at least partially overlaps with the wound opening area 26 and whose corresponding main emission direction 30 does not exceed a predetermined angular value, which preferably lies between 0° and 45°, with the depth extension direction X of the surgical wound 24. In FIG. 2, such an angle between a main emission direction 30 and the depth extension direction X of the surgical wound 24 is denoted by a by way of example. It can thereby be ensured that the surgical wound 24 is well illuminated in its entire depth also.

A common main emission direction, which extends, for example, along a central axis of the sum of all corresponding light cones, can also be assigned to the lighting devices 12 activated to illuminate the surgical wound 24. Via an adjusting device (not shown), the common main emission direction and/or corresponding main emission directions 30 can be changed to adapt the illumination to a changing surgery situation. For example, the beam paths of the lighting devices 12 can, for example, be focused on the wound opening area 26. In the course of such an adaptation, lighting devices 12 can also be deactivated or changed in their luminous flux, and/or lighting devices 12 that have hitherto not been used can be activated. To avoid reflections, which can emanate from the drape 22, the lighting devices 12 can be set such that the drape 22 is not illuminated, if at all possible.

The camera 16, which in the embodiment shown here is located in the immediate vicinity of a central lighting device 12, but could also be arranged in an outer region of the illumination device 10, is configured to monitor the region below the plurality of lighting devices 12.

The camera 16 is configured here to detect both the region of a surgical wound 24, as a result of which a region to be illuminated can be automatically determined, and to recognize gestures of a surgeon, in order thereby to change the orientation of the lighting devices 12 via the control device and the adjusting device, to detect objects that are located between the illumination device 10 and the surgical wound 24 to thus determine whether or which lighting devices 12 are to be changed in their luminous flux, and to determine changes in the illuminance of the surgical wound 24, so that the illuminance of the surgical wound 24 remains as constant as possible.

Both the depth extension direction X and the main emission directions 30 of the lighting devices 12 can be assigned coordinates or vectors in a spatial coordinate system X, Y, Z. As a result, for example, the angles between the main emission directions 30 and the depth extension direction X can be determined independently of a projection plane.

The lighting devices 12, which form the array 14, are attached to the ceiling of the operating room such that they are arranged in a position that is unchangeable relative to one another, but are variable in orientation (alignment of the corresponding light cone).

The illumination device 10 according to the invention thus allows good adaptation to any surgery situations, wherein, because the illumination device 10 substantially does not protrude from the ceiling of the operating room, the immediate surroundings above the patient can be better utilized by the surgeon or other surgical equipment.

The invention claimed is:

1. An illumination device for illuminating a surgical wound, which has a wound opening area on a surface of a body of a patient and extends into the body of the patient in a depth extension direction along a wound channel running into the body of the patient, wherein the illumination device comprises a control device with means for inputting information about a position of the wound opening area and the depth extension direction in a spatial coordinate system, wherein the illumination device has a plurality of lighting devices which are each configured to emit light in a main emission direction, and which each have at least one illuminant, wherein at least one of the lighting devices is configured to emit light such that an area illuminated by said at least one lighting device at least partially overlaps the wound opening area, wherein the main emission direction of each lighting device, which has an illuminated area at least partially overlapping with the wound opening area, and the depth extension direction of the surgical wound each enclose an angle with one another whose value does not exceed a predetermined angle value, wherein at least those lighting devices that have an illuminated area at least partially overlapping the wound opening area and whose corresponding main emission direction does not exceed a predetermined angular value with the depth extension direction of the surgical wound form an array, wherein the lighting devices in the array are arranged in an unchangeable position relative to one another.

2. The illumination device according to claim 1, wherein the control device is configured to control only those lighting devices of the illumination device that have an illuminated area at least partially overlapping the wound opening area, which lighting devices enclose an angle between their corresponding main emission direction and the depth extension direction of the surgical wound with one another, a value of which angle does not exceed the predetermined angle value.

3. The illumination device according to claim 1, wherein the illumination device comprises air passages which are configured to allow an air flow of an air-conditioning ceiling to which the illumination device is attached or in which the illumination device is integrated.

4. The illumination device according to claim 1, wherein the lighting devices comprise illuminants emitting light of different spectra and are configured to emit light in an adjustable spectral range by mixing the light emitted by the illuminants.

5. The illumination device according to claim 1, wherein the lighting devices can be set in their luminous flux.

6. The illumination device according to claim 1, wherein the lighting devices comprise reflectors and/or optical lenses and/or optical conversion media which are configured to focus and/or scatter and/or deflect light and/or to change light spectrally.

7. The illumination device according to claim 1, wherein the illumination device comprises an adjusting device which is configured to adjust the angle between the main emission direction of at least one lighting device and the depth extension direction of the surgical wound.

8. The illumination device according to claim 7, wherein the adjusting device comprises a camera which is configured to detect regions which are located in the main emission direction of at least one lighting device, and a determination unit, which is configured, based on the regions detected by the camera, to determine a surgical wound, wherein the adjusting device is configured to change the angle between the main emission direction of at least one lighting device and the depth extension direction-of the surgical wound.

9. The illumination device according to claim 7, wherein the adjusting device comprises a camera which is configured to detect gestures which a user of the illumination device carries out, and a determination unit, or is connected thereto, which is configured to assign the gestures to predetermined operating commands, wherein the adjusting device is configured to adjust an alignment of a corresponding main emission direction of lighting devices associated with the adjusting device based on the operating commands.

10. The illumination device according to claim 7, wherein the adjusting device comprises or is connected to a data interface which is configured to receive surgery data relating to a surgery to be carried out on a patient, wherein the adjusting device is configured to adjust an alignment of a corresponding main emission direction of lighting devices associated with the adjusting device based on the surgery data.

11. A method for illuminating a surgical wound, the method comprising the steps of:

providing a illumination device which has a plurality of lighting devices which are each configured to emit light in a main emission direction, wherein at least some of the lighting devices form an array in which the lighting devices are arranged at an unchangeable position relative to one another, inputting information about a position of a surgical wound in a spatial coordinate system which has a wound opening area on the surface of the body of a patient, determining a depth extension direction of the wound along a wound channel running into the body of the patient, determining at least one lighting device of the illumination device, which lighting device is configured to emit light such that an area illuminated by said at least one lighting device overlaps at least partially with the wound opening area, and that its main emission direction encloses an angle with the depth extension direction of the surgical wound, a value of which angle does not exceed a predetermined angular value, and activating the lighting devices determined in this way to illuminate the surgical wound.

12. The method according to claim 11, wherein the method further comprises:

setting the angle between the main emission direction of at least one lighting device and the depth extension direction of the surgical wound by pivoting a corresponding lighting device.

13. The method according to claim 11, wherein the method further comprises:

changing a luminous flux and/or an emission spectrum of at least one of the lighting devices.

14. The method according to claim 11, wherein the method further comprises:

detecting regions that are located in the main emission direction of at least one lighting device by a camera, determining information about the position of the surgical wound in the spatial coordinate system based on the regions detected by the camera, setting the angle between the main emission direction of at least one lighting device and the depth extension direction of the surgical wound.

15. The method according to claim 11, wherein the method further comprises:

providing a data interface via which data are passed on to the illumination device, inputting surgery data, on the basis of which a basic prediction of the position of the surgical wound in the spatial coordinate system is possible via the data interface to adjust an alignment of a corresponding main emission direction of at least one lighting device based on the surgery data.

* * * * *